US00PP14962P2

(12) United States Plant Patent
Rosborg

(10) Patent No.: US PP14,962 P2
(45) Date of Patent: Jun. 29, 2004

(54) KALANCHOE PLANT NAMED 'JAZZ'

(50) Latin Name: *Kalanchoe blossfeldiana*
Varietal Denomination: Jazz

(75) Inventor: Lars Rosborg, Odense (DK)

(73) Assignee: Gartneriet Rosborg Bellinge A/S, Odense (DK)

( * ) Notice: Subject to any disclaimer, the term of this patent is extended or adjusted under 35 U.S.C. 154(b) by 0 days.

(21) Appl. No.: 10/637,063

(22) Filed: Aug. 7, 2003

(51) Int. Cl.[7] ..... A01H 5/00
(52) U.S. Cl. ..... Plt./337
(58) Field of Search ..... Plt./337

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Kalanchoe plant named 'Jazz', characterized by its compact and upright plant habit; freely flowering habit; large red purple-colored flowers; uniform and stable flower color; dark green glossy leaves; and good postproduction longevity.

1 Drawing Sheet

Botanical classification/cultivar designation: *Kalanchoe blossfeldiana* cultivar Jazz.

BACKGROUND OF THE INVENTION

The present invention relates to a new and distinct cultivar of Kalanchoe plant, botanically known as *Kalanchoe blossfeldiana,* and hereinafter referred to by the name 'Jazz'.

The new Kalanchoe is a product of a planned breeding program conducted by the Inventor in Odense, Denmark. The objective of the breeding program was to create new Kalanchoe cultivars with attractive and stable flower color and good postproduction longevity.

The new Kalanchoe originated from a cross-pollination made by the Inventor in Odense, Denmark of a proprietary selection of Kalanchoe identified as code number 323/98, not patented, as the female, or seed, parent with a proprietary selection of Kalanchoe identified as code number 535/97-1, not patented, as the male, or pollen, parent. The new Kalanchoe was discovered and selected by the Inventor within the progeny of the stated cross-pollination in a controlled environment in Odense, Denmark during the spring of 2000. The selection of this plant was based on its attractive flower color.

Asexual reproduction of the new Kalanchoe by terminal cuttings taken at Odense, Denmark, has shown that the unique features of this new Kalanchoe are stable and reproduced true to type in successive generations.

BRIEF SUMMARY OF THE INVENTION

The cultivar Jazz has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Jazz'. These characteristics in combination distinguish 'Jazz' as a new and distinct cultivar:

1. Compact and upright plant habit.
2. Freely flowering habit.

3. Large red purple-colored flowers; flower color uniform and stable.
4. Dark green glossy leaves.
5. Good postproduction longevity.

Plants of the new Kalanchoe differ primarily from plants of the parent selections in flower color.

Plants of the new Kalanchoe can be compared to plants of the cultivar Cora, disclosed in U.S. Plant Pat. No. 11,479. In side-by-side comparisons conducted in Odense, Denmark, plants of the new Kalanchoe differed from plants of the cultivar Cora in the following characteristics:

1. Plants of the new Kalanchoe had larger leaves with shorter petioles than plants of the cultivar Cora.
2. Plants of the new Kalanchoe had darker green-colored leaves than plants of the cultivar Cora.
3. Flower color of plants of the new Kalanchoe was darker and more stable than flower color of plants of the cultivar Cora.

BRIEF DESCRIPTION OF THE PHOTOGRAPHS

The accompanying colored photographs illustrate the overall appearance of the new Kalanchoe, showing the colors as true as it is reasonably possible to obtain in colored reproductions of this type. Colors in the photographs differ slightly from the color values cited in the detailed botanical description which accurately describe the colors of the new Kalanchoe.

The photograph at the top of the sheet comprises a side perspective view of a typical potted plant of 'Jazz'.

The photograph at the bottom of the sheet comprises a top perspective view of a typical potted plant of 'Jazz'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and for the following observations and measurements were grown in Odense, Denmark, during the winter under commercial practice in a glass-covered greenhouse for about 14 to 18 weeks in 10.5-cm containers. Plants were exposed to photoinductive short day/long night conditions for the last 10 weeks of production. During the production of the plants, day and night temperatures averaged 20 and 18° C., respectively. Plants used in the photographs and description were not pinched.

Botanical classification: *Kalanchoe blossfeldiana* cultivar Jazz.

Parentage:

*Female, or seed, parent.*—Proprietary selection of *Kalanchoe blossfeldiana* identified as code number 323/98, not patented.

*Male, or pollen, parent.*—Proprietary selection of *Kalanchoe blossfeldiana* identified as code number 535/97-1, not patented.

Propagation:

*Type cutting.*—Terminal cuttings.

*Time to initiate roots, summer and winter.*—About 11 days at 20° C.

*Root description.*—Fibrous, fine; well-branched.

Plant description:

*Form.*—Compact and upright plant habit with rounded crown. Plants are appropriate for 10.5-cm containers.

*Branching habit.*—Freely branching, about five or six lateral branches develop. Pinching (removal of terminal apex) is not required but will enhance lateral branch development.

*Plant height at flowering.*—About 20 cm.

*Plant diameter at flowering.*—About 24 cm.

*Lateral branch length.*—About 14.8 cm.

*Internode length.*—About 1.5 cm.

*Stem texture.*—Smooth, glabrous.

*Stem color.*—146A to 146B.

Foliage description: Unless otherwise specified, the foliage description represents leaves from a vegetative plant.

*Arrangement.*—Simple, opposite.

*Size, vegetative plants.*—Length: About 13.1 cm. Width: About 8.1 cm.

*Size, reproductive plants.*—Length: About 10.5 cm. Width: About 5.4 cm.

*Shape.*—Oval to oblong.

*Apex.*—Rounded.

*Base.*—Obtuse.

*Margin.*—Deeply crenate.

*Aspect.*—Initially slight concave, then convex.

*Texture, upper and lower surfaces.*—Leathery; glabrous; succluent.

*Venation pattern.*—Pinnate.

*Color.*—Young foliage, upper surface: 137A. Young foliage, lower surface: 137C. Fully expanded foliage, upper surface: 139A; glossy. Fully expanded foliage, lower surface: 146A. Venation, upper and lower surfaces: Same as lamina color.

*Petiole.*—Length: About 2.3 cm. Diameter: About 7 mm. Texture: Smooth, glabrous. Color, upper and lower surfaces: 137C.

Flower description:

*Flower type and habit.*—Single flowers arranged in rounded compound dischasial cymes that arise from leaf axils; flowers face mostly upright. Freely flowering, about 250 to 300 flowers will develop per plant. Flowers persistent. Flowers not fragrant.

*Natural flowering season.*—Late autumn/winter/early spring. Flower initiation and development can be induced under photoinductive short day/long night conditions.

*Time to flower.*—About 9.5 to 11 weeks of photoinductive short day/long night conditions are required to produce flowering plants.

*Flower opening.*—First flower open is the terminal flower at the main axis and is followed by the opening of the terminal flowers of the side branches of the inflorescence.

*Post-production longevity.*—Flowers of plants of the new Kalanchoe maintain good substance for about five to six weeks under greenhouse conditions.

*Cyme height.*—About 10.2 cm.

*Cyme diameter.*—About 7.1 cm.

*Number of flowers and flower buds per cyme.*—About 70.

*Flower diameter.*—About 2 cm.

*Flower depth (height).*—About 1.5 cm.

*Flower buds.*—Shape: Oblong. Length: About 1.4 cm. Width: About 4.5 mm. Color: 194A.

*Petals.*—Quantity: Four fused at base. Length: About 9 mm. Diameter: About 8 mm. Shape: Rounded oval. Apex: Acute. Margin: Entire. Texture, upper and lower surfaces: Smooth, glabrous. Color: When opening, upper surface: 68A. When opening, lower surface: 62D, towards the margins, 62A. Fully opened, upper surface: 68B; color becoming closer to 68C with development. Fully opened, lower surface: 62C, towards the margins, 62B.

*Sepals.*—Quantity: Four fused at base. Length: About 1.1 cm. Diameter: About 3 mm. Shape: Ovate to oblong. Apex: Acute. Margin: Entire. Texture, upper and lower surfaces: Smooth, glabrous. Color, immature, upper and lower surfaces: 138A. Color, mature, upper and lower surfaces: 138A.

*Peduncles.*—Length: About 9.8 cm. Diameter: About 4 mm. Angle: Mostly erect. Strength: Strong. Texture: Smooth, glabrous. Color: 146A.

*Pedicels.*—Length: About 2 to 3 mm. Diameter: About 1 mm. Angle: About 40° from vertical. Strength: Strong. Texture: Smooth, glabrous. Color: 146B.

*Reproductive organs.*—Stamens: Stamen number: Eight per flower. Anther shape: Oval. Anther length: About 1 mm. Anther color: Yellow green. Pollen amount: Scarce. Pollen color: Yellow. Pistils: Pistil number: Four per flower. Style color: Light green. Stigma shape: Round. Stigma color: Light green. Ovaries: Superior and four-celled. Ovary color: 138A.

*Seed/fruit.*—Seed and fruit production has not been observed.

Disease/pest resistance: Plants of the new Kalanchoe have been observed to be resistant to Powdery Mildew. Resistance to known Kalanchoe pests has not been observed on plants of the new Kalanchoe grown under commercial greenhouse conditions.

It is claimed:

1. A new and distinct cultivar of Kalanchoe plant named 'Jazz', as illustrated and described.

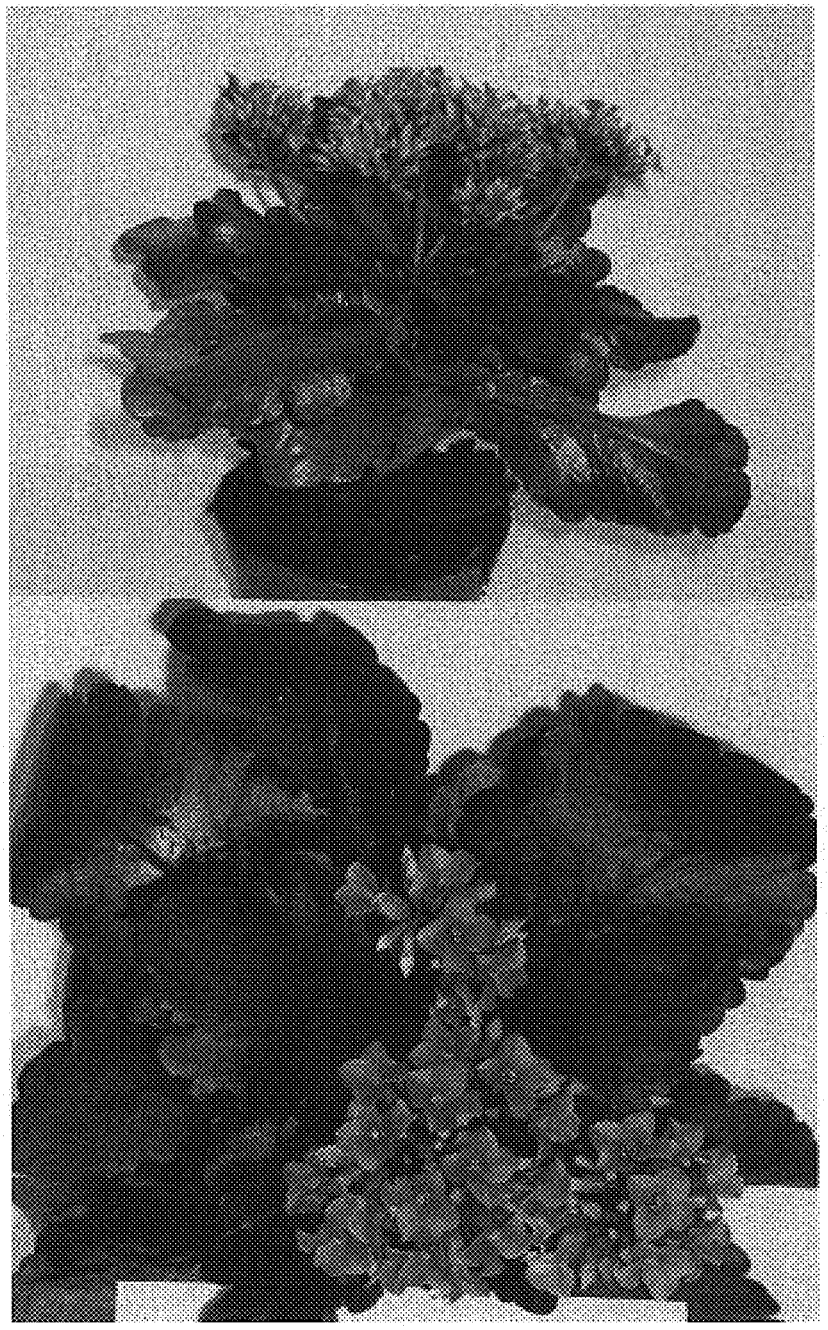

* * * * *